United States Patent [19]

Baus et al.

[11] Patent Number: 4,987,143
[45] Date of Patent: Jan. 22, 1991

[54] 1-HYDROXY-1,2,4-TRIAZOLE COMPOUNDS USEFUL AS FUNGICIDES

[75] Inventors: Ulf Baus, Dossenheim; Wolfgang Reuther, Heidelberg; Gisela Lorenz, Neustadt; Eberhard Ammermann, Ludwigshafen, all of Fed. Rep. of Germany

[73] Assignee: Basf Aktiengesellschaft, Ludwigshafen, Fed. Rep. of Germany

[21] Appl. No.: 480,143

[22] Filed: Feb. 14, 1990

[30] Foreign Application Priority Data

Mar. 3, 1989 [DE] Fed. Rep. of Germany ....... 3906771

[51] Int. Cl.$^5$ .................. A01N 43/653; C07D 249/08
[52] U.S. Cl. ..................................... 514/383; 548/101; 548/262.2; 548/267.8; 548/268.6; 514/184
[58] Field of Search .................. 548/267.8, 101, 268.6, 548/262.2; 514/383, 184

[56] References Cited

U.S. PATENT DOCUMENTS 4,532,341 7/1985 Holmwood et al. ................. 549/559
4,734,126 3/1988 Holmwood et al. .................... 71/92

OTHER PUBLICATIONS

Morrell et al., "Fungi Colonizing Redwood, Etc.", Wood and Fiber Sci., 20 (1988), pp. 243-249.
Wazny et al., "The Reflectance Method for, etc.", Wood Sci. Technol. 23 (1989), pp. 179-189.

Primary Examiner—Glennon H. Hollrah
Assistant Examiner—Patricia L. Morris
Attorney, Agent, or Firm—Oblon, Spivak, McClelland, Maier & Neustadt

[57] ABSTRACT

Compounds of the general formula

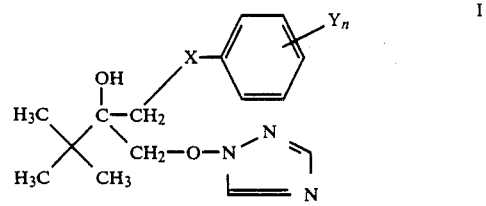

where X is $CH_2$ or O, Y is hydrogen, alkyl, alkoxy, halogen, aryl or aryloxy and n is from 1 to 5, and their salts and complexes, and fungicides containing these compounds.

4 Claims, No Drawings

1-HYDROXY-1,2,4-TRIAZOLE COMPOUNDS USEFUL AS FUNGICIDES

The present invention relates to novel N-hydroxytriazole derivatives, their salts and metal complexes, a process for their preparation and their use as fungicides.

It is known that triazolyl derivatives, for example 1-(4-chlorophenyl)-3-(1,2,4-triazol-1-ylmethyl)-4,4-dimethylpentan-3-ol (DE-30 18 866), can be used as fungicides. However, its action is not satisfactory in all cases.

We have found that compounds of the general formula I

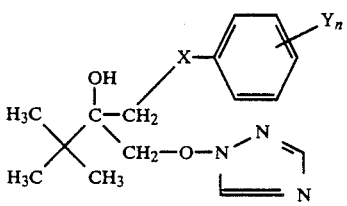

where
X is $CH_2$ or O, Y is hydrogen, $C_1$–$C_9$-alkyl, $C_1$–$C_4$-alkoxy, halogen, aryl or aryloxy and n is from 1 to 5, and their salts and complexes have a surprisingly good fungicidal action.

Y is, for example, $C_1$–$C_9$-alkyl, in particular $C_1$–$C_4$-alkyl (methyl, ethyl, tert-butyl, pentyl, hexyl, heptyl, octyl or nonyl), $C_1$–$C_4$-alkoxy (methoxy, ethoxy or tert-butoxy), halogen (Cl, Br or F), aryl (phenyl) or aryloxy (phenoxy).

n is, for example, 1, 2, 3, 4 or 5 and, where n is greater than 1, the radicals Y may be identical or different, for example 3-chloro-4-methyl. Salts are, for example, the plant-tolerated addition salts with acids, for example the salts with inorganic or organic acids, such as the salts of hydrochloric acid, hydrobromic acid, nitric acid, oxalic acid, acetic acid, sulfuric acid, phosphoric acid or dodecylbenzenesulfonic acid. The activity of the salts is attributable to the cation, so that in general any anion may be chosen.

Furthermore, the compounds of the formula I can be converted into metal complexes by known methods. This may be effected by reacting the compounds with metal salts, for example salts of the metals copper, zinc, iron, manganese or nickel, e.g. copper(II) chloride, zinc(II) chloride, iron(III) chloride, copper(II) nitrate, manganese(II) chloride or nickel(II) bromide.

We have also found that the compounds of the general formula I can be prepared very readily and in good yields, for example by reacting 1-hydroxy-1,2,4-triazole with a compound of the general formula II

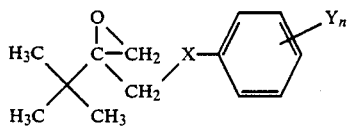

where X, Y and n have the abovementioned meanings.

The reaction is carried out, for example, in an inert organic solvent, such as tetrahydrofuran (THF), dimethyl sulfoxide (DMSO), dimethylformamide (DMF) or diethyl ether, preferably THF or a THF/water mixture, in the presence of a base, such as triethylamine, tributylamine, NaOH, sodium carbonate or pyridine, at from 0° to 100° C., preferably at room temperature (20° C.). The compounds of the general formula I are formed as racemates, which can be separated into their isomers in a conventional manner. Both the pure enantiomers and mixtures thereof form the subject of the invention and can be used as fungicides.

The compounds of the general formula II are known or can be prepared by known processes (for example EP No. 0 040 345). 1-Hydroxy-1,2,4-triazole can be prepared as follows:

103.5 g (1.5 mol) of 1-H-1,2,4-triazole were dissolved in 1,344 g (12 mol) of 50% strength aqueous potassium hydroxide. While cooling with ice, 340 g (3 mol) of 30% strength $H_2O_2$ and, a little at a time, 555 g (3.75 mol) of phthalic anhydride were added and the mixture was stirred for 2 hours at room temperature (from 20° to 30° C.). Thereafter, it was acidified to a pH of less than 1.5 with about 35% strength sulfuric acid, the resulting precipitate was filtered off under suction and the filtrate was worked up in a conventional manner. 19 g (15% of theory) of 1-hydroxy-1,2,4-triazole of melting point 132° C. were obtained.

PREPARATION EXAMPLE 1.7 g (20 mmol) of 1-hydroxy-1,2,4-triazole are dissolved in 10 ml of n-butanol. 4.81 g (20 mmol) of 2-(4-chlorophenoxymethyl)-2-tert-butyloxirane are added while stirring. The solution is refluxed for several hours, after which it is taken up in ethyl acetate/ether, the solution is washed with water and the organic phase is dried. After removal of the solvent, 5.8 g (93% of theory) of an oily crude product are obtained (compound No. 1).

$C_{15}H_{20}OClN_3O_2$ calculated: C 58.1 H 6.5 C 11.4 N 13.5 (309.61)

HNMR ($CDCl_3$): 1.09 (s, 9H); 4.17 (dd, 2H); 4.62 (dd, 2H); 6.8–7.32 (m, 4H); 7.76 (s, 1H); 8.01 (s, 1H).

In general, the novel compounds have excellent activity against a broad spectrum of phytopathogenic fungi, in particular from the class consisting of the ascomycetes and basidiomycetes. Some of them possess systemic activity and can be used as foliage fungicides and soil fungicides.

The fungicidal compounds are of particular interest for controlling a large number of fungi of various crops or their seeds, in particular wheat, rye, barley, oats, rice, corn, lawns, cotton, soybean, coffee, sugar cane, fruit and ornamentals in horticulture, in viticulture and in vegetables, such as cucumber, beans and the cucurbitaceae.

The novel compounds are particularly suitable for controlling the following plant diseases:
*Erysiphe graminis* (powdery mildew) in cereals,
*Erysiphe cichoracearum* and *Sphaerotheca fuliginea* on cucurbitaceae,
*Podosphaera leucotricha* on apples,
*Uncinula necator* on grapevines,
*Puccinia* species on cereals,
*Rhizoctonia* species on cotton and lawns,
*Ustilago* species on cereals and sugar cane,
*Venturia inaequalis* (scab) on apples,
*Helminthosporium* species on cereals,
*Septoria nodorum* on wheat,
*Botrytis cinerea* (grey mold) on strawberries and grapevines,

*Cercospora arachidicola* on peanuts,
*Pseudocercosporella herpotrichoides* on wheat and cereals,
*Pyricularia oryzae* on rice,
*Phytophthora infestans* on potatoes and tomatoes,
Fusarium and Verticillium species on various plants,
*Plasmopara viticola* on grapevines and
Alternaria species on vegetables and fruit.

The compounds are used by spraying or dusting the plants with the active ingredients or treating the seeds of the plants with the active ingredients. They are used before or after infection of the plants or seeds by the fungi.

The novel substances can be converted into the conventional formulations, such as solutions, emulsions, suspensions, dusts, powders, pastes and granules. The application forms depend entirely on the intended uses; they should in any case ensure fine and uniform distribution of the active substance. The formulations are prepared in a known manner, for example by extending the active ingredient with solvents and/or carriers, with or without the use of emulsifiers and dispersants, and, where water is used as a diluent, it is also possible to use other organic solvents as auxiliary solvents. Suitable auxiliaries for this purpose are essentially: solvents, such as aromatics (e.g. xylene), chlorinated aromatics (e.g. chlorobenzenes), paraffins (e.g. oil fractions), alcohols (e.g. methanol or butanol), ketones (e.g. cyclohexanone), amines (e.g. ethanolamine or dimethylformamide) and water; carriers, such as ground natural minerals (for example kaolins, clay, talc or chalk) and ground synthetic minerals (for example finely divided silica or silicates); emulsifiers, such as nonionic and anionic emulsifiers (for example polyoxyethylene fatty alcohol ethers, alkylsulfonates and arylsulfonates) and dispersants, such as ligninsulfite waste liquors and methylcellulose.

The fungicides contain in general from 0.1 to 95, preferably from 0.5 to 90, % by weight of active ingredient.

The application rates are from 0.02 to 3 kg or more of active ingredient per ha, depending on the type of effect desired. The novel compounds can also be used in material protection, for example against *Paecilomyces variotii*.

The agents or the ready-to-use formulations prepared therefrom, such as solutions, emulsions, suspensions, powders, dusts, pastes or granules, are used in a known manner, for example by spraying, atomizing, dusting, broadcasting, dressing or pouring.

Examples of such formulations are:
I. 90 parts by weight of compound No. 1 are mixed with 10 parts by weight of N-methyl-α-pyrrolidone, and a solution which is suitable for use in the form of very small drops is obtained.
II. 20 parts by weight of compound No. 1 are dissolved in a mixture which consists of 80 parts by weight of xylene, 10 parts by weight of the adduct of from 8 to 10 moles of ethylene oxide with 1 mole of oleic acid N-monoethanolamide, 5 parts by weight of calcium salt of dodecylbenzenesulfonic acid and 5 parts by weight of the adduct of 40 moles of ethylene oxide with 1 mole of castor oil. An aqueous dispersion is obtained by pouring the solution into water and finely distributing it in the water.
III. 20 parts by weight of compound No. 1 are dissolved in a mixture which consists of 40 parts by weight of cyclohexanone, 30 parts by weight of isobutanol and 20 parts by weight of the adduct of 40 moles of ethylene oxide with 1 mole of castor oil. An aqueous dispersion is obtained by pouring the solution into water and finely distributing it in the water.
IV. 20 parts by weight of compound No. 1 are dissolved in a mixture which consists of 25 parts by weight of cyclohexanol, 65 parts by weight of a mineral oil fraction boiling within a range from 210° to 280° C. and 10 parts by weight of the adduct of 40 moles of ethylene oxide with 1 mole of castor oil. An aqueous dispersion is obtained by pouring the solution into water and finely distributing it in the water.
V. 80 parts by weight of compound No. 1 are thoroughly mixed with 3 parts by weight of the sodium salt of diisobutylnaphthalene-α-sulfonic acid, 10 parts by weight of the sodium salt of a ligninsulfonic acid from a sulfite waste liquor and 7 parts by weight of silica gel powder, and the mixture is milled in a hammer mill. A spray liquor is obtained by finely distributing the mixture in water.
VI. 3 parts by weight of compound No. 1 are thoroughly mixed with 97 parts by weight of finely divided kaolin. A dust which contains 3% by weight of the active ingredient is obtained in this manner.
VII. 30 parts by weight of compound No. 1 are thoroughly mixed with a mixture of 92 parts by weight of silica gel powder and 8 parts by weight of liquid paraffin, which has been sprayed onto the surface of this silica gel. A formulation of the active ingredient having good adhesion is obtained in this manner.
VIII. 40 parts by weight of compound No 1 are thoroughly mixed with 10 parts by weight of the sodium salt of a phenolsulfonic acid/urea/formaldehyde condensate, 2 parts by weight of silica gel and 48 parts by weight of water. A stable aqueous dispersion is obtained. Dilution with water gives an aqueous dispersion.
IX. 20 parts by weight of compound No. 1 are thoroughly mixed with 2 parts by weight of the calcium salt of dodecylbenzenesulfonic acid, 8 parts by weight of a fatty alcohol polyglycol ether, 2 parts by weight of the sodium salt of a phenolsulfonic acid/urea/-formaldehyde condensate and 68 parts by weight of a paraffinic mineral oil A stable oily dispersion is obtained.

In these application forms, the novel agents may also be present together with other active ingredients, for example herbicides, insecticides, growth regulators and fungicides, or may be mixed with fertilizers and applied. Mixing with fungicides gives a broader fungicidal action spectrum in many cases.

EXAMPLE OF USE

Activity against wheat mildew

Leaves of wheat seedlings of the Kanzler variety grown in pots were sprayed with aqueous spray liquor which contained 80% of active ingredient and 20% of emulsifier in the dry substance and, 24 hours after the spray coat had dried, were dusted with oidia (spores) of wheat mildew (*Erysiphe graminis* var. tritici). The test plants were then placed in a greenhouse at from 20° to 22° C. and from 75 to 80% relative humidity. After 7 days, the extent of the development of mildew was determined.

The result shows that active ingredient 1 has a good fungicidal action (100%) when used as 0.0125% strength by weight spray liquor.

We claim:

1. A compound of the formula (I):

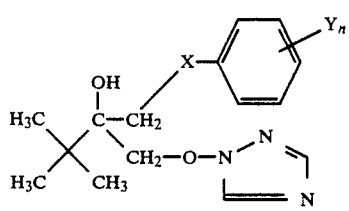

where

X is CH$_2$ or O,

Y is hydrogen, alkyl of 1 to 9 carbon atoms, C$_1$–C$_4$-alkoxy, halogen, phenyl or phenoxy, and n is from 1 to 5, and acid addition salts thereof, wherein the acid is selected from the group consisting of hydrochloric acid, hydrobromic acid, nitric acid, oxalic acid, acetic acid, sulfuric acid, phosphoric acid, and dodecylbenzenesulfonic acid, and metal complexes thereof, wherein the metal is selected from the group consisting of copper, zinc, iron, maganese, and nickel.

2. A compound of the formula I as claimed in claim 1, wherein X is O and Y$_n$ is 4-chloro.

3. A fungicidal composition which contains a carrier and a fungicidally effective amount of a compound of the formula (I):

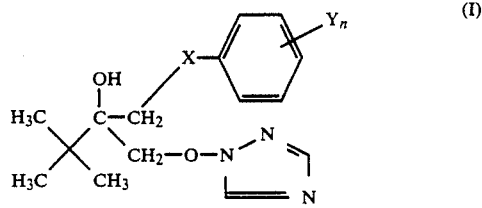

where

X is CH$_2$ or O

Y is hydrogen, alkyl of 1 to 9 carbon atoms, C$_1$–C$_4$-alkoxy, halogen, phenyl or phenoxy, n is from 1 to 5, and a fungicidally-acceptable salt or metal complex thereof.

4. A method for controlling fungi, wherein the fungi or the plants, seeds, wood or planted areas threatened by fungal attack are treated with a fungicidally effective amount of a compound of the formula (I):

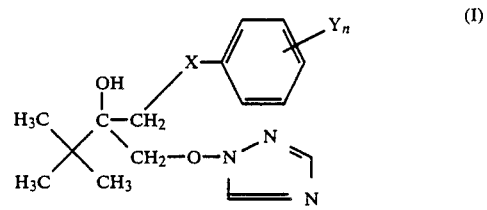

where

X is CH$_2$ or O,

Y is hydrogen, alkyl of 1 to 9 carbon atoms, C$_1$–C$_4$-alkoxy, halogen, phenyl or phenoxy, n is from 1 to 5, and a fungicidally-acceptable acid addition salt or metal complex thereof.

* * * * *